United States Patent
Eichner et al.

(10) Patent No.: US 9,315,450 B2
(45) Date of Patent: Apr. 19, 2016

(54) DESFESOTERODINE SALTS

(71) Applicant: ratiopharm GmbH, Ulm (DE)

(72) Inventors: Simone Eichner, Neu-ulm (DE); Wolfgang Albrecht, Ulm (DE)

(73) Assignee: ratiopharm GmbH, Ulm (DE)

( * ) Notice: Subject to any disclaimer, the term of this patent is extended or adjusted under 35 U.S.C. 154(b) by 0 days.

(21) Appl. No.: 14/406,649

(22) PCT Filed: Jun. 14, 2013

(86) PCT No.: PCT/US2013/045992
§ 371 (c)(1),
(2) Date: Dec. 9, 2014

(87) PCT Pub. No.: WO2013/188829
PCT Pub. Date: Dec. 19, 2013

(65) Prior Publication Data
US 2015/0152044 A1    Jun. 4, 2015

Related U.S. Application Data

(60) Provisional application No. 61/659,829, filed on Jun. 14, 2012, provisional application No. 61/818,135, filed on May 1, 2013.

(51) Int. Cl.
*A61K 31/315* (2006.01)
*C07C 215/54* (2006.01)
*C07C 55/10* (2006.01)
*C07C 59/245* (2006.01)

(52) U.S. Cl.
CPC .............. *C07C 215/54* (2013.01); *C07C 55/10* (2013.01); *C07C 59/245* (2013.01)

(58) Field of Classification Search
CPC ..... A61K 31/315; C07C 215/54; C07C 55/10
USPC ........................................... 514/648; 560/138
See application file for complete search history.

(56) References Cited

U.S. PATENT DOCUMENTS 5,559,269 A    9/1996  Johansson et al.
6,809,214 B2   10/2004 Meese

FOREIGN PATENT DOCUMENTS

| | | |
|---|---|---|
| EP | 1077912 | 5/1999 |
| WO | WO 2007/138440 | 12/2007 |
| WO | WO 2010/0013039 | 2/2010 |
| WO | WO 2010/0130392 | 11/2010 |
| WO | WO 2011/158257 | 12/2011 |

*Primary Examiner* — Raymond Henley, III
(74) *Attorney, Agent, or Firm* — Baker & Hostetler LLP

(57) ABSTRACT

The invention relates to substantially pure Desfesoterodine salts, Desfesoterodine salts, solid state forms thereof and pharmaceutical compositions comprising one or more of the Desfesoterodine salts and/or solid state forms thereof.

27 Claims, 6 Drawing Sheets

DESFESOTERODINE SALTS

CROSS-REFERENCE TO RELATED APPLICATIONS

This application is the National Stage of International Application No. PCT/US2013/045992, filed Jun. 14, 2013, which claims the benefit of priority of U.S. Provisional Application No. 61/659,829, filed Jun. 14, 2012 and U.S. Provisional Application No. 61/818,135, filed May 1, 2013, the entire disclosures of which are incorporated herein by reference.

FIELD OF THE INVENTION

The present invention encompasses substantially pure Desfesoterodine salts, Desfesoterodine salts, solid state forms thereof and pharmaceutical compositions comprising one or more of the Desfesoterodine salts and/or solid state forms thereof.

BACKGROUND OF THE INVENTION

Desfesoterodine, (R)-(+)-2-(3-diisopropylamino-1-phenylpropyl)-4-hydroxymethyl-phenol, having the following formula:

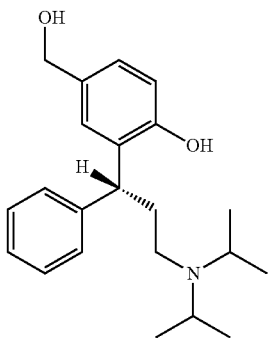

is the active metabolite and the key intermediate in the preparation of tolterodine and fesoterodine. These compounds possess M3—Muscarinic antagonist activity and have been used as a treatment for urinary incontinence and overactive bladder.

Desfesoterodine, as well as certain pharmaceutically acceptable salts thereof, are described in WO2007/138440, U.S. Pat. No. 5,559,269, U.S. Pat. No. 6,809,214 and EP1077912.

WO2010/0130392 describes the tartrate salt of Desfesoterodine.

Different salts and solid state forms of an active pharmaceutical ingredient may possess different properties. Such variations in the properties of different salts may provide a basis for improving formulation, for example, by facilitating better processing or handling characteristics, improving the dissolution profile, or improving stability and shelf-life. These variations in the properties of different salts may also provide improvements to the final dosage form, for instance, if they serve to improve bioavailability. Different salts of an active pharmaceutical ingredient may also give rise to a variety of polymorphs or crystalline forms, which may in turn provide additional opportunities to assess and use variations in the properties and characteristics of a solid active pharmaceutical ingredient.

Polymorphism, the occurrence of different crystal forms, is a property of some molecules and molecular complexes. A single molecule may give rise to a variety of polymorphs having distinct crystal structures and physical properties like melting point, thermal behaviors (e.g. measured by thermogravimetric analysis—"TGA", or differential scanning calorimetry—"DSC"), X-ray diffraction pattern, infrared absorption fingerprint, raman fingerprint and solid state NMR spectrum. One or more of these techniques may be used to distinguish different polymorphic forms of a compound.

Discovering new salts and solid state forms of a pharmaceutical product can provide materials having desirable processing properties, such as ease of handling, ease of processing, storage stability, ease of purification or as desirable intermediate crystal forms that facilitate conversion to other polymorphic forms. New salts and solid state forms of a pharmaceutically useful compound can also provide an opportunity to improve the performance characteristics of a pharmaceutical product. It enlarges the repertoire of materials that a formulation scientist has available for formulation optimization, for example by providing a product with different properties, e.g., better processing or handling characteristics, or improved shelf-life. For at least these reasons, there is a need for additional salts and solid state forms of Desfesoterodine.

SUMMARY OF THE INVENTION

The present invention provides substantially pure Desfesoterodine salts, salts of Desfesoterodine, solid state forms thereof, and pharmaceutical compositions and/or formulations comprising at least one of the salts or solid state forms.

The present invention also encompasses the use of any one of the Desfesoterodine salts and solid state forms of the present invention for the preparation of other Desfesoterodine salts, or of Desfesoterodine base, solid state forms and/or formulations thereof.

The present invention also encompasses the Desfesoterodine salts and solid state forms described herein for use as medicaments, particularly for the treatment of urinary incontinence and overactive bladder.

The present invention also encompasses a process for the preparation of pharmaceutical formulations comprising combining any one or a combination of the Desfesoterodine salts and solid state forms, or a pharmaceutical composition comprising said Desfesoterodine salts and solid state forms, and at least one pharmaceutically acceptable excipient.

The present invention also encompasses a method of treating a person suffering from urinary incontinence and overactive bladder, comprising administering a therapeutically effective amount of any one or a combination of the Desfesoterodine salts and solid state forms, or a pharmaceutical composition and/or formulation comprising any one or more of the forms of Desfesoterodine salts described herein.

DETAILED DESCRIPTION OF THE INVENTION

Figure 1:
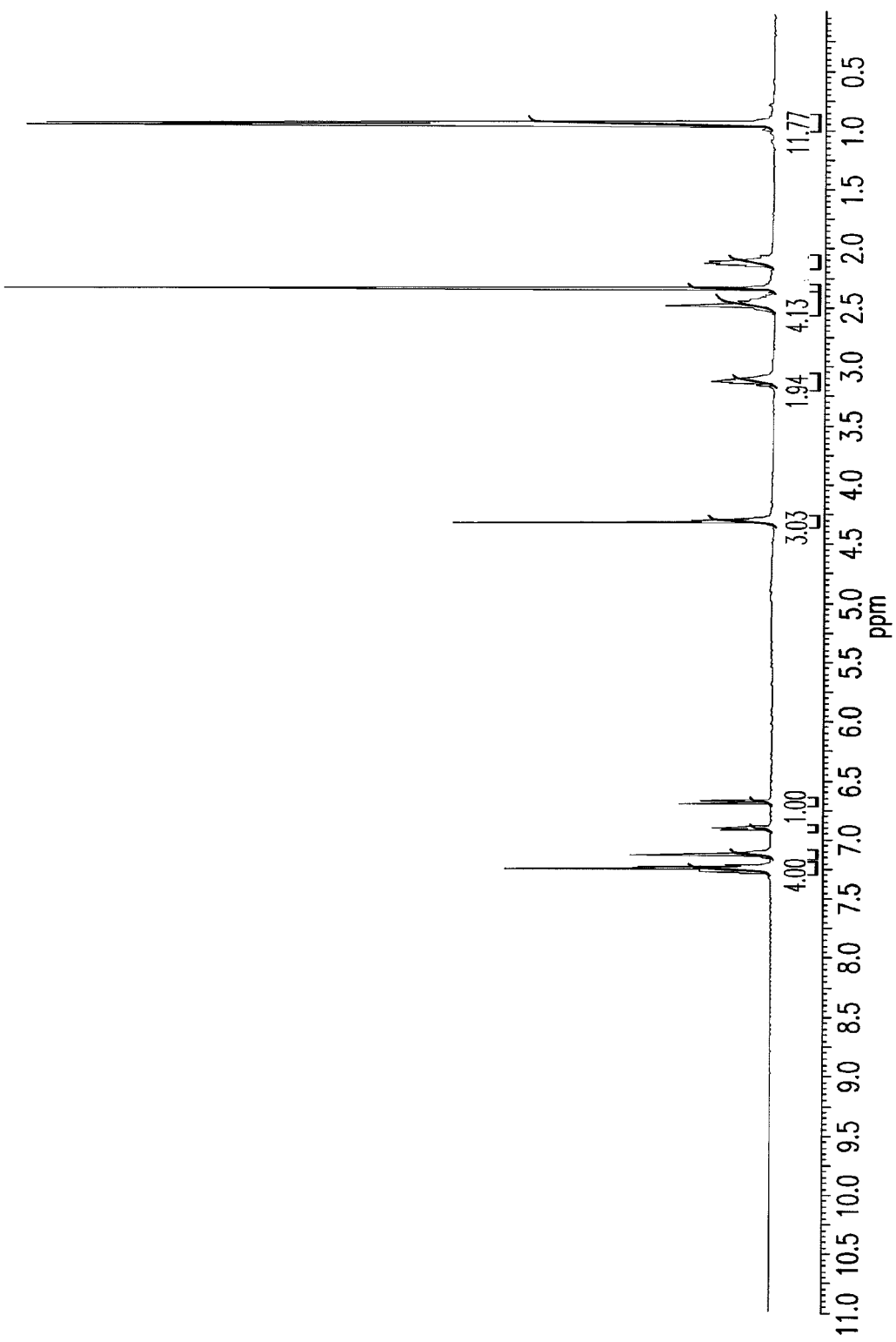
FIG. 1 shows a $^1$H-NMR spectrum of Desfesoterodine succinate.

The present invention encompasses Desfesoterodine salts, solid state forms thereof and pharmaceutical compositions comprising one or more of the Desfesoterodine salts and/or solid state forms thereof. In some embodiments said Desfesoterodine salts or solid state forms thereof are provided in substantially pure form.

Solid state properties of Desfesoterodine salts can be influenced by controlling the conditions under which the salts, e.g., Desfesoterodine succinate, is obtained in solid form.

As used herein, the term "ester impurity" refers to the general formula

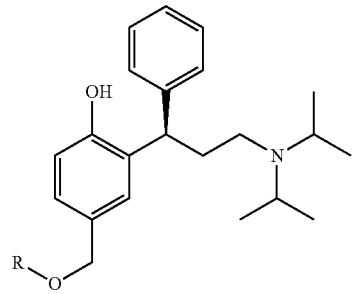

with R corresponding to the organic acid, which forms an ester bond between the carboxylic group of the acid and the 5-hydroxymethyl group of Desfesoterodine.

Examples of the ester impurity include at least one of the following.

The related ester impurity that might be generated in Desfesoterodine succinate, can be Succinic acid mono-[3-((R)-3-diisopropylamino-1-phenyl-propyl)-4-hydroxybenzyl]ester (structure shown below, also referred to as to '(R)-4-((3-(3-(diisopropylamino)-1-phenylpropyl)-4-hydroxybenzyl)oxy)-4-oxobutanoic acid').

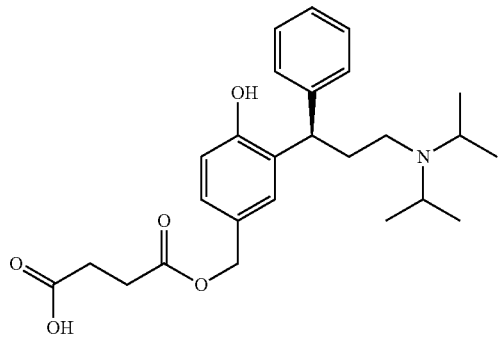 [SMILES: CC(C)N(CC[C@H](c1ccccc1)c1cc(COC(=O)CCC(=O)O)ccc1O)C(C)C]

The related ester impurity that might be generated in Desfesoterodine L-malate, can be either (S)-2-Hydroxy-succinic acid 1-[3-((R)-3-diisopropylamino-1-phenylpropyl)-4-hydroxy-benzyl]ester (structure shown below left, also referred to as to '(S)-4-((3-((R)-3-(diisopropylamino)-1-phenylpropyl)-4-hydroxybenzyl)oxy)-3-hydroxy-4-oxobutanoic acid') or (S)-2-Hydroxy-succinic acid 4-[3-((R)-3-diisopropylamino-1-phenyl-propyl)-4-hydroxy-benzyl]ester (structure shown below right, also referred to as '(S)-4-((3-((R)-3-(di-isopropylamino)-1-phenylpropyl)-4-hydroxybenzyl)oxy)-2-hydroxy-4-oxobutanoic acid').

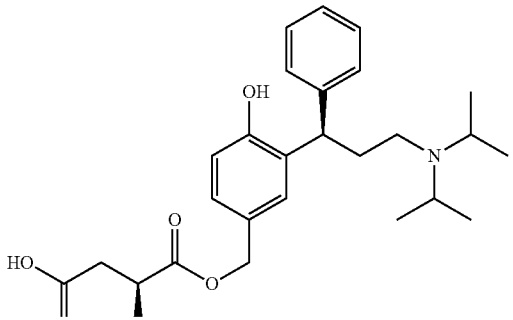

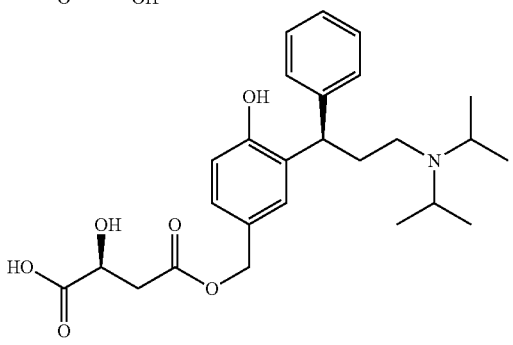

As used herein, the term "substantially pure desfesoterodine salt" means that the Desfesoterodine salt contains less than 0.5%, preferably less than 0.1%, most preferably less than 0.05% of the corresponding ester impurity, as measured by HPLC.

Preferably, the Desfesoterodine salt also has a low residual solvent content. By "low residual solvent content" is meant that the solvent, for example, ethanol, isopropanol, butanol, acetone, ethyl acetate, acetonitrile or tetrahydrofuran, preferably acetone or isopropanol, is present in an amount of less than 5,000 ppm, preferably less than 2,000 ppm, more preferably, less than 1,000 ppm, most preferably less than 500 ppm. e.g. "low residual solvent content" is meant that the solvent is present in an amount of about 500 ppm to about 5000 ppm, preferably of about 500 ppm to about 2000 ppm, more preferably of about 500 ppm to about 1000 ppm, most preferably of about 1000 to about 2000 ppm.

As used herein, and unless indicated otherwise, the term "pure Desfesoterodine salt" refers to the essentially chemically pure molecule of the Desfesoterodine salt. Essentially chemically pure in the context of the present invention means a chemical purity of at least 95%, >98%, >98.5% or even >99%, as measured by HPLC (area %, detection at 220 nm).

The purity of the Desfesoterodine salt can be determined by HPLC.

The HPLC analytical methods are designed to use UV absorption at a given wavelength for recording the presence and the amount of a compound in a sample passing the detector at any given point in time. For example, the primary output of any HPLC run with standard equipment will be an area percentage of the respective peak in the UV detection chromatogram, i.e., the area under the curve (AUC). Particularly in the absence of any detailed information on specific extinction coefficients of the compound(s) present in a sample, the percent area values obtained by HPLC are typically equated with a "% by weight" value without applying any correction factor. For example, the AUC percent value for a single peak (eluted at a certain retention time) is assumed to correspond to the percent proportion of the compound by weight.

As used herein, the term "reference standard" refers to a compound that may be used both for quantitative and qualitative analysis of an active pharmaceutical ingredient. For example, the retention time of the compound in HPLC allows for setting a relative retention time, thus making qualitative analysis possible. The concentration of the compound in solution before injection into an HPLC column allows for comparison of the areas under the peaks in an HPLC chromatogram, thus making quantitative analysis possible.

Although some of the knowledge of those in the art regarding reference standards has been described in general terms up to this point, those skilled in the art also understand that the detector response can be, for example, the peak heights or integrated peak areas of a chromatogram obtained, e.g. by UV or refractive index detection, from the eluent of an HPLC system or, e.g. flame ionization detection or thermal conductivity detection, from the eluent of a gas chromatograph, or other detector response, e.g. the UV absorbance, of spots on a fluorescent TLC plate. The position of the reference standard may be used to calculate e.g. the relative retention time for the compound and other impurities.

In some embodiments, the salts of Desfesoterodine of the invention are substantially free of any other salts of Desfesoterodine, and the solid state forms of the invention are substantially free of any other polymorphic forms, or of specified polymorphic forms. In any embodiment of the present invention, by "substantially free" is meant that the forms of the present invention contain 20% (w/w) or less, 10% (w/w) or less, 5% (w/w) or less, 2% (w/w) or less, particularly 1% (w/w) or less, more particularly 0.5% (w/w) or less, and most particularly 0.2% (w/w) or less of any other salts, polymorphs or of a specified polymorph of Desfesoterodine salt.

A crystal form may be referred to herein as being characterized by graphical data "substantially as depicted in" a Figure. Such data include, for example, powder X-ray diffractograms and solid state NMR spectra. As is well-known in the art, the graphical data potentially provides additional technical information to further define the respective solid state form (a so-called "fingerprint") which can not necessarily be described by reference to numerical values or peak positions alone. In any event, the skilled person will understand that such graphical representations of data may be subject to small variations, e.g., in peak relative intensities and peak positions due to factors such as variations in instrument response and variations in sample concentration and purity, which are well known to the skilled person. Nonetheless, the skilled person would readily be capable of comparing the graphical data in the Figures herein with graphical data generated for an unknown crystal form and confirm whether the two sets of graphical data are characterizing the same crystal form or two different crystal forms. A crystal form of a Desfesoterodine salt referred to herein as being characterized by graphical data "substantially as depicted in" a Figure will thus be understood to include any crystal forms of the Desfesoterodine salt characterized with the graphical data having such small variations, as are well known to the skilled person, in comparison with the Figure.

As used herein, the term "isolated" in reference to any of the Desfesoterodine salts or solid state forms thereof of the present invention corresponds to Desfesoterodine salt or solid state form thereof that is physically separated from the reaction mixture where it is formed.

As used herein, unless stated otherwise, the XRPD measurements are taken using copper Kα radiation wavelength (1.5418 Å).

As used herein, and unless stated otherwise, the term "anhydrous" in relation to any of the crystalline Desfesoterodine salts relates to a crystalline Desfesoterodine salt which contains not more than 1.5% (w/w), or not more than 1% (w/w), or not more than 0.5% (w/w) of either water or organic solvents (bound and unbound) as measured by TGA or by Karl Fisher titration, for example, a Desfesoterodine salt which contains between about 0% to about 1.5% (w/w) or between about 0% to about 1% (w/w) or between about 0% to about 0.5% (w/w) of either water or organic solvents as measured by TGA or by Karl Fischer titration.

As used herein and unless indicated otherwise, the term "solvate" refers to a crystal form that incorporates a solvent in the crystal structure. When the solvent is water, the solvate is often referred to as a "hydrate." The solvent in a solvate may be present in either a stoichiometric or in a non-stoichiometric amount.

A thing, e.g., a reaction mixture, may be characterized herein as being at, or allowed to come to "room temperature," often abbreviated "RT." This means that the temperature of the thing is close to, or the same as, that of the space, e.g., the room or fume hood, in which the thing is located. Typically, room temperature is from about 20° C. to about 30° C., or about 22° C. to about 27° C., or about 25° C.

A process or step may be referred to herein as being carried out "overnight." This refers to a time interval, e.g., for the process or step, that spans the time during the night, when that process or step may not be actively observed. This time interval is from about 8 to about 20 hours, or about 10-18 hours, typically about 16 hours.

As used herein, the term "reduced pressure" refers to a pressure of about 10 mbar to about 50 mbar.

As used herein, the terms "vol." or "volume" can be used to refer to ml per gram of the corresponding Desfesoterodine. For example, a statement that 0.5 g of Desfesoterodine is dissolved in ten volumes of a Solvent X would be understood to mean that the 0.5 g of Desfesoterodine was dissolved in 5 ml of Solvent X.

In the course of preparing several salts of Desfesoterodine provided herein, the formation of an ester impurity was observed during the work-up of the salts. Examples of this impurity are described above (e.g., formation of (2R,3R)-2,3-dihydroxy succinic acid mono-[3-((R)-3-diisopropylamino-1-phenylpropyl)-4-hydroxybenzyl]ester as an impurity in desfesoterodine L-tartrate salt. This corresponding ester impurity is however present in the salts of the present invention in very low levels if at all.

It was further observed that attempts to remove residual organic solvents to an acceptable level in accordance with pharmaceutical quality requirements by performing techniques commonly applied in the art, failed to yield the desired results. Moreover, attempts to reduce the residual organic solvents to an acceptable level by applying more drastic techniques known in the art, such as drying under high vacuum at elevated temperatures for extended periods of time, also failed due to the significant increase in the amount of the corresponding ester impurity. The salt of the present invention, in particular, the succiante salt contain both very low levels of residual solvents as well as of the ester impurity.

The present invention provides Desfesoterodine salts, preferably in substantially pure form. The above salts can be isolated. Preferably, the above salts can be in a solid form.

In particular, the present invention comprises Desfesoterodine succinate. The Desfesoterodine succinate salt may be characterized by an ¹H-NMR spectrum substantially as depicted in FIG. 1. The molar ratio between Desfesoterodine and succinic acid can be 1:1 to 1:1.5, preferably about 1:1, respectively.

The succinate salt of desfesoterodine can be in an anhydrous form.

The succinate salt of desfesoterodine can be prepared as a substantially pure Desfesoterodine salt which may also serve as a suitable substitute of the known compound fesoterodine fumarate due to its favorable aqueous solubility profile. Preferably, Desfesoterodine succinate has a chemical purity of at least 95%, >98%, or even >99% (by HPLC).

Figure 5:
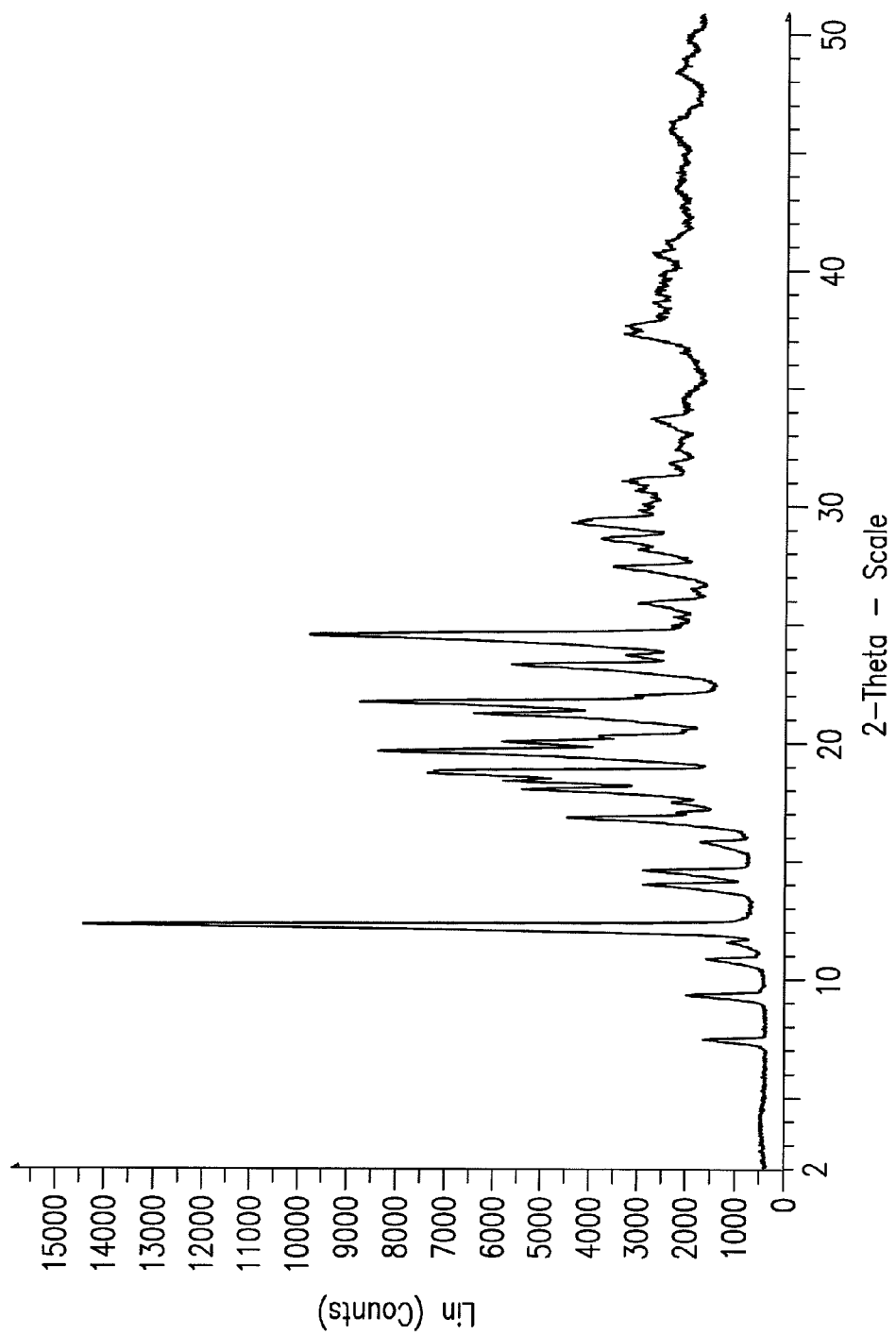
FIG. 5 shows a X-ray powder diffractogram of Desfesoterodine succinate Form S1.

The Desfesoterodine succinate may be in a crystalline form. According to one embodiment, the present invention comprises a crystalline form of Desfesoterodine succinate, designated as Form S1. Crystalline form S1 of Desfesoterodine succinate salt can be characterized by data selected from one or more of the following: an X-ray powder diffraction pattern having peaks at 7.4, 16.8, 18.0, 21.7 and 27.4 degrees two theta±0.2 degrees two theta; an X-ray powder diffraction pattern substantially as depicted in FIG. 5; and combinations thereof.

Figure 3:
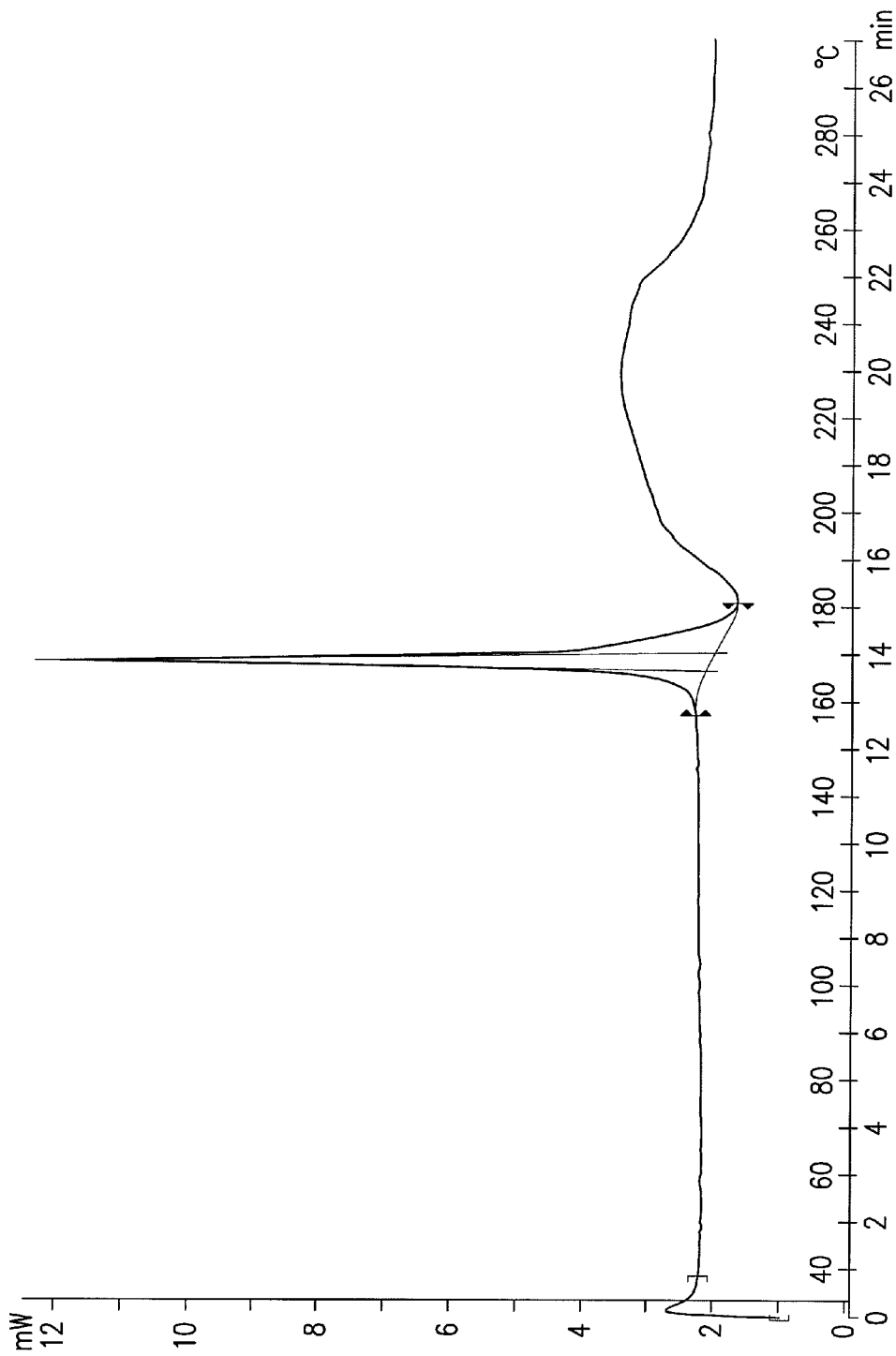
FIG. 3 shows a DSC thermogram of Desfesoterodine succinate.

Crystalline Form S1 of Desfesoterodine succinate may be characterized by an X-ray powder diffraction pattern having peaks at 7.4, 16.8, 18.0, 21.7 and 27.4 degrees two theta±0.2 degrees two theta. It may be further characterized by data selected from: an X-ray powder diffraction pattern having any one, two, three, four or five additional peaks selected from peaks at 9.3, 12.2, 14.6, 19.6 and 24.5 degrees two theta±0.2 degrees two theta; a DSC curve having an endothermic peak at about 169° C.±2, a DSC curve substantially as depicted in FIG. 3; and combinations thereof.

Crystalline Form S1 of Desfesoterodine succinate can be anhydrous.

Crystalline Form S1 of Desfesoterodine succinate can also be characterized by any combination of the above data.

Figure 2:
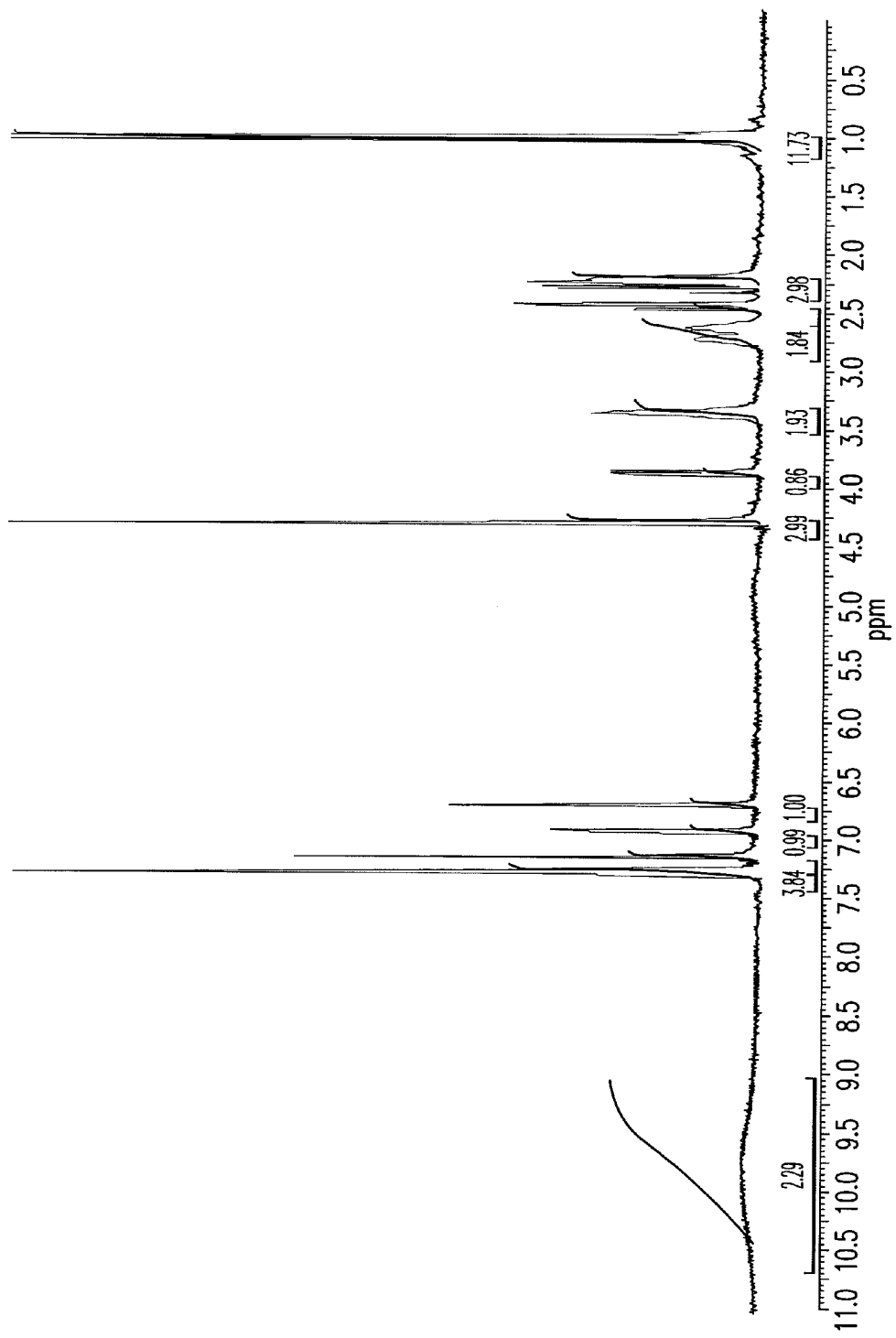
FIG. 2 shows a $^1$H-NMR spectrum of Desfesoterodine L-malate.

In another embodiment, the present invention comprises a Desfesoterodine malate salt. The Desfesoterodine malate salt may be characterized by an ¹H-NMR spectrum substantially as depicted in FIG. 2. The molar ratio between Desfesoterodine to malic acid can be 1:1 to 1:1.5, preferably about 1:1. The malate salt can be for example the L-malate salt or the D-malate salt. Preferably the malate salt is the L-malate salt.

Preferably, Desfesoterodine malate has a chemical purity of at least 95%, >98%, or even >99% (by HPLC).

Figure 6:
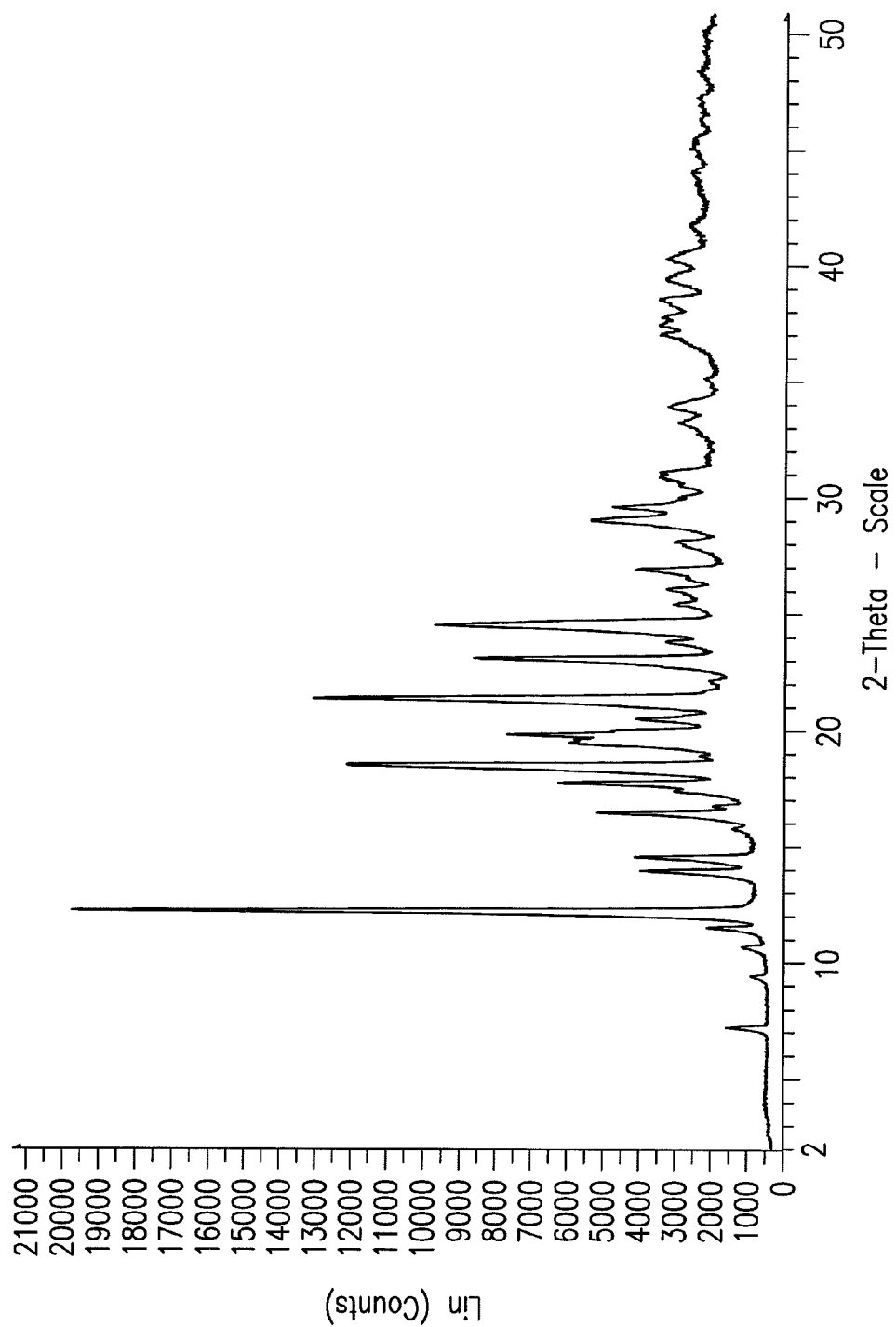
FIG. 6 shows an X-ray powder diffractogram of Desfesoterodine L-malate Form M1.

The Desfesoterodine L-malate may be in crystalline form. The present invention comprises a crystalline form of Desfesoterodine L-malate, designated as Form M1. Crystalline form M1 of Desfesoterodine L-malate salt can be characterized by data selected from one or more of the following: an X-ray powder diffraction pattern having peaks at 7.2, 16.4, 19.8, 21.3 and 29.6 degrees two theta±0.2 degrees two theta; an X-ray powder diffraction pattern substantially as depicted in FIG. 6; and combinations thereof.

Figure 4:
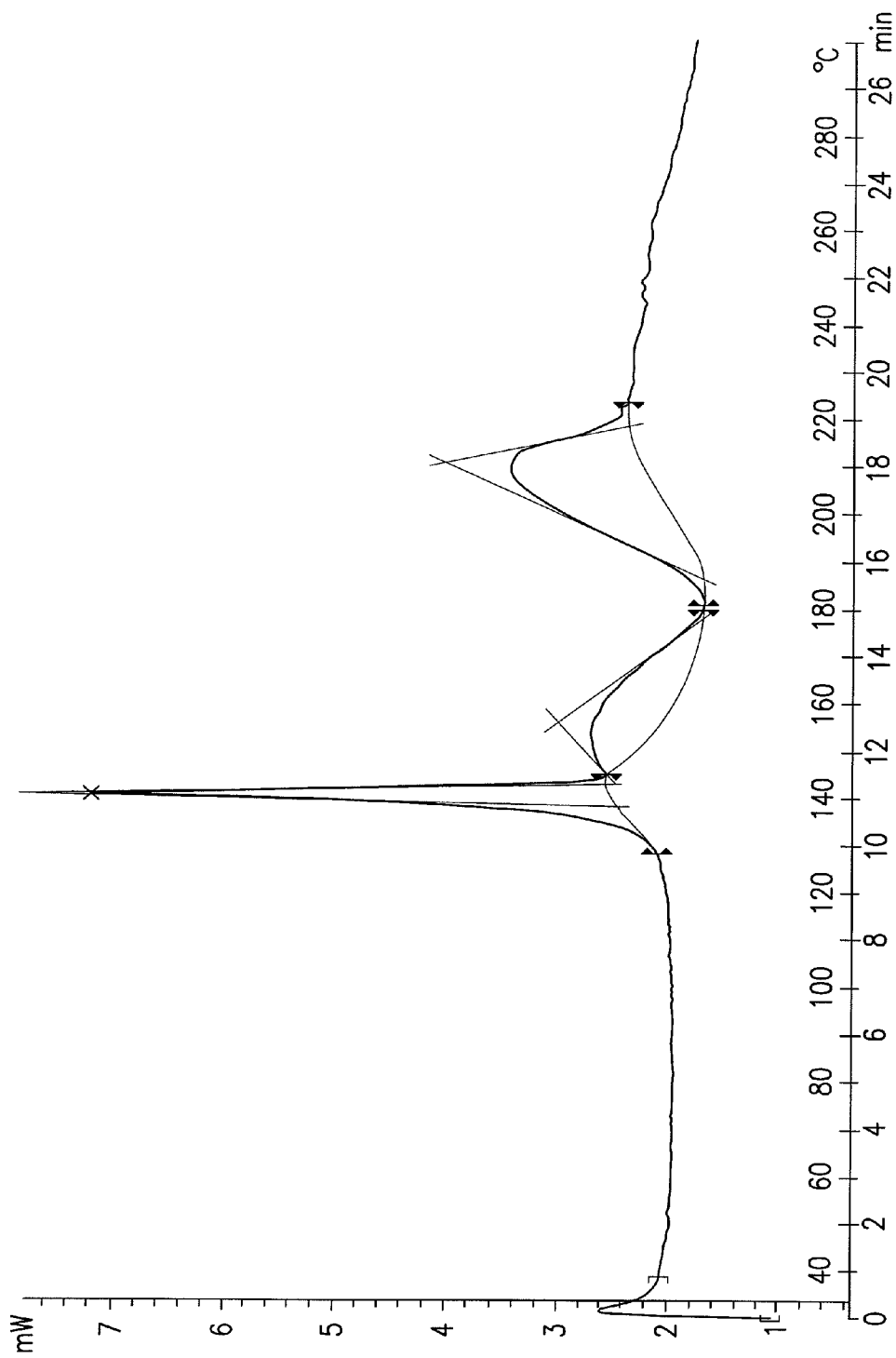
FIG. 4 shows a DSC thermogram of Desfesoterodine L-malate.

Crystalline Form M1 of Desfesoterodine L-malate may be characterized by an X-ray powder diffraction pattern having peaks at 7.2, 16.4, 19.8, 21.3 and 29.6 degrees two theta±0.2 degrees two theta. It may be further characterized by data selected from an X-ray powder diffraction pattern having any one, two, three, four or five additional peaks at 12.2, 14.5, 18.5, 23.1 and 24.5 degrees two theta±0.2 degrees two theta; a DSC curve having an endothermic peak at about 141° C., or a DSC curve substantially as depicted in FIG. 4; and combinations thereof.

Crystalline Form M1 of Desfesoterodine L-malate can also be characterized by any combination of the above data.

The described salts and solid state forms can be used to prepare Desfesoterodine base or other different salts of Desfesoterodine, as well as solid state forms thereof and/or pharmaceutical formulations comprising one or more of the salts and/or solid state forms thereof.

The present invention also encompasses a process for preparing other Desfesoterodine salts. The process comprises preparing any one of the described Desfesoterodine salts and solid state forms thereof, particularly the succinate and malate salts, by the processes of the present invention, and converting that salt to said other Desfesoterodine salt. The conversion can be done, for example, by a process comprising basifying any one, or a combination of the above described Desfesoterodine salts and/or solid state forms thereof, and reacting the obtained Desfesoterodine base with a suitable acid, to obtain the corresponding salt of desfesoterodine. Alternatively, the conversion can be achieved by salt switching, i.e., reacting a first Desfesoterodine salt with an acid having a $pK_a$ which is lower than the $pK_a$ of the acid of said first Desfesoterodine salt.

The Desfesoterodine salts and/or solid state forms thereof of the present invention can also be used as a medicament, preferably for the treatment of a person suffering from urinary incontinence and overactive bladder.

The present invention further encompasses 1) a pharmaceutical composition comprising any one or a combination of the Desfesoterodine salts and solid state forms thereof, as described herein; 2) a pharmaceutical formulation comprising any one or a combination of the Desfesoterodine salts and solid state forms thereof, as described herein, and at least one pharmaceutically acceptable excipient; and 3) a process to prepare such formulations comprising combining any one or a combination of the Desfesoterodine salts and solid state forms, or pharmaceutical compositions and at least one pharmaceutically acceptable excipient; 4) the use of any one or combination of the above-described Desfesoterodine salts and solid state forms thereof in the manufacture of a pharmaceutical composition, and 5) a method of treating a person suffering from urinary incontinence and overactive bladder, comprising administering a therapeutically effective amount of a pharmaceutical composition or formulation comprising any one or more of the Desfesoterodine salts and solid state forms as described herein.

Having thus described the invention with reference to particular preferred embodiments and illustrative examples, those in the art will appreciate that there are modifications to the invention as described and illustrated which do not depart from the spirit and scope of the invention as disclosed in the specification and appended claims. The Examples are set forth to aid in understanding the invention but are not intended to, and should not be construed to limit its scope in any way.

ANALYTICAL METHODS

¹H-NMR Spectroscopy
The instrument was a Varian Mercury 400 Plus NMR Spectrometer, Oxford AS, 400 MHz.
HPLC/UV
Instrument: UPLC Agilent 1290
Column: Reprosil-Pur Basic C18; 5 μm; 125×4.6 mm
Column temp.: 35° C.
Flow [mL/min]: 1
Injection volume: 5 μL
Solvent A: 20 mM $KH_2PO_4$, pH 3.0
Solvent B: Acetonitrile Gradient:

| time [min] | Solvent A [%] |
|---|---|
| 0 | 75 |
| 14 | 51 |
| 15 | 30 |
| 17 | 30 |
| 18 | 75 |
| 20 | 75 |

Detection: UV ($\lambda$=220 nm)
  HPLC/MS
HPLC
instrument: Agilent 1200
column: Phenomenex Kinetex C18; 2.6 µm; 150×4.6 mm
flow: 0.7 ml/min.
temperature: 40° C.
eluent
A: Acetonitrile
B: acetonitrile+0.2% formic acid+0.1% heptafluoro butyric acid
Gradient:

|  | Time [min] | eluent A [%] | eluent B [%] |
|---|---|---|---|
|  | 0.0 | 30 | 70 |
|  | 14.0 | 85 | 15 |
|  | 17.0 | 95 | 5 |
|  | 19.0 | 95 | 5 |
|  | 20.0 | 30 | 70 |
| Stop time | 25.0 |  |  | injection volume: 5 µl
  Mass Spectrometry
instrument: Bruker HCT
Mass range mode: Ultrascan
Ion polarity: Positive
Ion Source type: ESI
HV capillary: 4500 V
Nebulizer gas: 65 psi
Dry Gas: 8 l/min.
Temperature: 320° C.
Trap Drive: 74.9
scan [m/z] 105-800 atomic mass units (amu)
  Differential Scanning Calorimetry (DSC)
Instrument: Mettler Toledo DSC 822E coupled with a Mettler Toledo Gas-Flow-Controller TS0800GC1 (Mettler-Toledo GmbH, Gießen, Germany)
Aluminium crucible: 40 µL
Lid: Perforated
Temperature range: 30° C. to 300° C.
Heating rate: 10° C./min
Nitrogen flush: 50 mL/min
Software: STARe Version. 8.10
Interpretation: Endothermic modus
  X-Ray Powder Diffraction (XRPD)
The sample was analyzed on a D8 Advance X-ray powder diffractometer (Bruker-AXS, Karlsruhe, Germany). The sample holder was rotated in a plane parallel to its surface at 20 rpm during the measurement. Further conditions for the measurements are summarized in the table below. The raw data were analyzed with the program EVA (Bruker-AXS, Germany). The samples were layered onto a silicon specimen holder.

|  | standard measurement |
|---|---|
| Radiation | Cu K$_\alpha$ ($\lambda$ = 1.5418 Å) |
| Source | 38 kV/40 mA |
| Detector | Vantec |
| detector slit | Variable |
| divergence slit | v6 |
| antiscattering slit | v6 |
| 2θ range/° | 2 ≤ 2θ ≤ 55 |
| step size/° | 0.017 |

Determination of Residual Solvent Content by Headspace GC-MS
Headspace sampler
instrument: Agilent G 1888
oven: 70° C.
loop: 100° C.
transfer line: 120° C.
vial equilibration: 15 min
pressure: 0.2 min.
loop fill: 0.2 min.
inject time: 0.5 min.
  GC-MS
instruments
GC: Agilent 7890A
MSD: Agilent 5975C
method: HS EP 35.M
column: Agilent DB-624 30 m×250 µm×1.4 µm
temperature program: 35° C., 5 min isothermal
  35-190° C., 5° C./min
  190° C., 9.4 min isothermal
run time: 45.4 min
carrier gas: helium flow: 12.9 ml/min
pressure: 12.4 psi
injection: split split ratio:10:1
temperature: inlet: 220° C.
  GC-MS interface: 280° C.
  MS source: 230° C.
  MS quad.: 150° C.
MSD pressure: 9.8×10$^{-6}$ Torr (SI 1.3×10$^{-3}$ Pa)
tune file: atune.u
emission: 34.6 µA
electron energy: 69.9 eV
repeller: 27.8 V
ion focus: 90.2 V
entrance lence: 25.5 V
EM volts: 1129.4 V
solvent delay: 2.5 min
scan: 35-500 m/z
Sample Preparation
  Into the headspace vial, 23-53 mg of the sample was dissolved in 1 ml DMSO and this solution was directly subjected to Headspace-GC-MS analysis.
  Quantification of the residual solvent content (here: acetone) was based on single point calibrations. For each sample to be analysed, a standard solution was prepared which contained acetone in an amount which corresponded to a value of 5,000 ppm. E.g. for quantification of the residual solvent content in a sample of 50.84 mg desfesoterodine succinate, a standard solution with 254 µg/ml acetone was prepared as follows: 325 µl (254 mg) acetone were added to 10 ml DMSO (conc.=25.4 mg/ml). 100 µl of this stock solution was diluted with 900 µl DMSO (→conc.=2.54 mg/ml) followed by another 1:10 dilution (→conc.=254 µg/ml).

EXAMPLES

Example 1

Preparation of Desfesoterodine Succinate

Desfesoterodine base (505 mg, 1.48 mmol) was suspended in 10 mL acetone and heated to 50° C. The resulting solution was cooled to 40° C. In a separate flask, succinic acid (175 mg, 1.48 mmol, 1.0 eq.) was suspended in 20 mL acetone and heated to 50° C. The temperature of the resulting solution was kept at 40° C. while the Desfesoterodine solution was added. The solution was cooled to 25° C. and stirred overnight. The obtained precipitate was filtered off, washed with 5 mL acetone and dried under normal pressure at 25° C. to yield 555 mg of Desfesoterodine succinate as a white powder (purity 99.63%).

Example 2

Preparation of Desfesoterodine Succinate

Desfesoterodine base (1.02 g, 2.9 mmol) was suspended in 20 mL acetone and heated to 50° C. The resulting solution was cooled to 40° C. In a separate flask, succinic acid (334 mg, 2.8 mmol, 0.95 eq.) was suspended in 30 mL acetone and heated to 50° C. The temperature of the resulting solution was kept at 40° C. while the Desfesoterodine solution was added. The solution was cooled to 25° C. and stirred overnight. The obtained precipitate was filtered off, washed with 5 mL acetone and dried under normal pressure at 25° C. to yield 1,030 mg of Desfesoterodine succinate as a white powder (purity 99.7%, residual content of acetone 2596 ppm).

Example 3

Preparation of Desfesoterodine Succinate

Desfesoterodine base (20.03 g, 58.6 mmol) was suspended in 200 mL acetone and heated to 50° C. The resulting solution was cooled to 40° C. In a separate flask, succinic acid (6.60 g, 55.6 mmol, 0.95 eq.) was suspended in 300 mL acetone and heated to 50° C. The temperature of the resulting solution was kept at 40° C. while the Desfesoterodine solution was added. The solution was cooled to 25° C. and stirred overnight. The obtained precipitate was filtered off, washed with 5 mL acetone and dried under normal pressure at 25° C. to yield 23.67 g of Desfesoterodine succinate as a white powder. (purity 99.82%, residual content of acetone 1406 ppm).

Example 4

Preparation of Desfesoterodine L-Malate

Desfesoterodine base (501 mg, 1.5 mmol) was suspended in 10 mL acetone and heated to 50° C. The resulting solution was cooled to 40° C. L-malic acid (193 mg, 1.5 mmol, 1 eq.) was suspended in 20 mL acetone and heated to 50° C. The resulting solution was maintained at 40° C. while Desfesoterodine was added. The solution was then cooled to 25° C., transferred into a refrigerator (4-6° C.) and stored for 3 days. Thereafter, the volume was reduced to 10 mL, and the solution stored for another 30 days in the refrigerator until precipitation was observed. The solid was then filtered off, washed with 10 mL acetone and dried under normal pressure at 25° C. to yield: 212 mg Desfesoterodine L-malate as a white powder. (purity 99.18%).

Example 5

Preparation of Desfesoterodine Succinate

Desfesoterodine base (1 g, 2.9 mmol) was suspended in either 13 ml acetone or 17 ml ethyl acetate. Dissolution was achieved by heating to 50° C. (acetone) or 68° C. (ethyl acetate). In a separate flask, succinic acid (about 0.95 to 1.10 eq) was suspended in 26 ml acetone or 34 ml ethyl acetate. Dissolution was achieved by heating to 50° C. (acetone) or 68° C. (ethyl acetate). The temperature of the succinic acid solution was kept at 50° C./68° C. while the Desfesoterodine solution was added. When the addition was completed, the solution was cooled to 25° C. and stirred for 5 hours (acetone) or 13 hours (ethyl acetate). The obtained precipitate was filtered off, washed with 10 ml acetone or 5 ml ethyl acetate and dried either under vacuo (40° C./17 mbar), leading to a product with a purity of 99.92%, residual content of ethylacetate 1006 ppm) or a purity of 99.84%, residual content of acetone 1001 ppm.

Example 6

Preparation of Desfesoterodine Succinate

The procedure of Example 5 was applied with the following modifications: 10.0 g (29.3 mmol) Desfesoterodine in 170 ml ethyl acetate; 3.5 g (29.3 mmol, 1 eq.) succinic acid in 340 ml ethyl acetate, heated to 65° C.; addition over 30 minutes at 53° C.; after addition the mixture was stirred at 25° C. for 13 hours; washing after filtration with 5 ml ethyl acetate; resulting solid was dried in vacuo (40° C./17 mbar) until a constant weight is reached. Yield: 12.3 g Desfesoterodine succinate (yield 91.4%). (purity 99.90%, residual content of ethylacetate 1003 ppm).

Example 7

Preparation of Desfesoterodine Succinate

The procedure of Example 5 was applied with the following modifications: 10.0 g (29.3 mmol) Desfesoterodine in 130 ml acetone; 3.5 g (29.3 mmol, 1 eq.) succinic acid in 260 ml acetone; after addition the mixture was stirred at 25° C. for 72 hours; washing after filtration with 10 ml acetone; resulting solid was dried in vacuo (40° C./17 mbar) until a constant weight is reached. Yield: 11.0 g Desfesoterodine succinate (yield 81.7%). (purity 99.92%, residual content of acetone 1000 ppm).

Example 8

Preparation of Desfesoterodine Succinate

The procedure of Example 5 was applied with the following modifications: 60.0 g (175.7 mmol) Desfesoterodine in 600 ml acetone; 20.75 g (175.7 mmol, 1 eq.) succinic acid in 1000 ml acetone; after addition the mixture was stirred at 25° C. for 18 hours; washing after filtration with 50 ml acetone; resulting solid was dried in vacuo (40° C./17 mbar) until a constant weight is reached. Yield: 73.06 g Desfesoterodine succinate (yield 90.4%). (purity 99.91%, residual content of acetone 1008 ppm).

Example 9

Preparation of Desfesoterodine Base

Preparation of Benzyl Tolterodine (HMT-I) from Tolterodine Tartrate

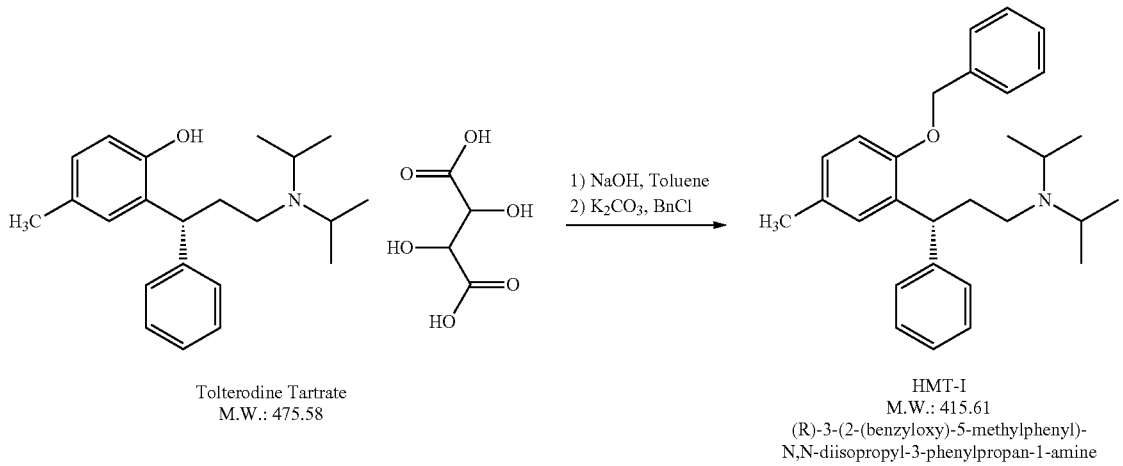

Tolterodine Tartrate
M.W.: 475.58

HMT-I
M.W.: 415.61
(R)-3-(2-(benzyloxy)-5-methylphenyl)-
N,N-diisopropyl-3-phenylpropan-1-amine Water (55 L) was charged into the reactor followed by sodium hydroxide (2.75 Kg) and allowed to stir until a clear solution was obtained. Toluene (77 L) and tolterodine tartrate (11.0 Kg) were charged to the reactor and stirred for 1 h at 30-35° C.; layers were separated. Aqueous layer was extracted with toluene (33.0 L). Combined organic layers were distilled out at 70° C. under reduced pressure followed by removal of traces of toluene by DMF (5.5 L) distillation to get an oily mass. Oil was dissolved in DMF (38.5 L). Potassium carbonate (9.57 Kg) was charged and temperature was increased to 65° C. Benzyl chloride (3.22 Kg) was added into the reaction mass and allowed to stir at 65° C. After completion; reaction mass was allowed to cool 30° C.; inorganic sludge was filtered out and washed with DMF (22 L). Combined organic filtrates were allowed to cool at 10° C. Water (~7.5 L) was added slowly maintaining temp 10° C. until turbidity appeared; seeding (55 g) was applied and reaction mass was allowed to stir for 1 h followed by addition of remaining water (55 L) at 10° C. Reaction mass was allowed to stir for 10 h between 5-10° C. for complete crystallization. Solid was filtered out and washed with precooled mixture of DMF (5.5 L) and water (5.5 L) and was dried under reduced pressure for about 6 h at 35° C. Dry (10.2 Kg).

Alternative Process for the Preparation of Benzyl olterodine (HMT-I) from Tolterodine Tartrate

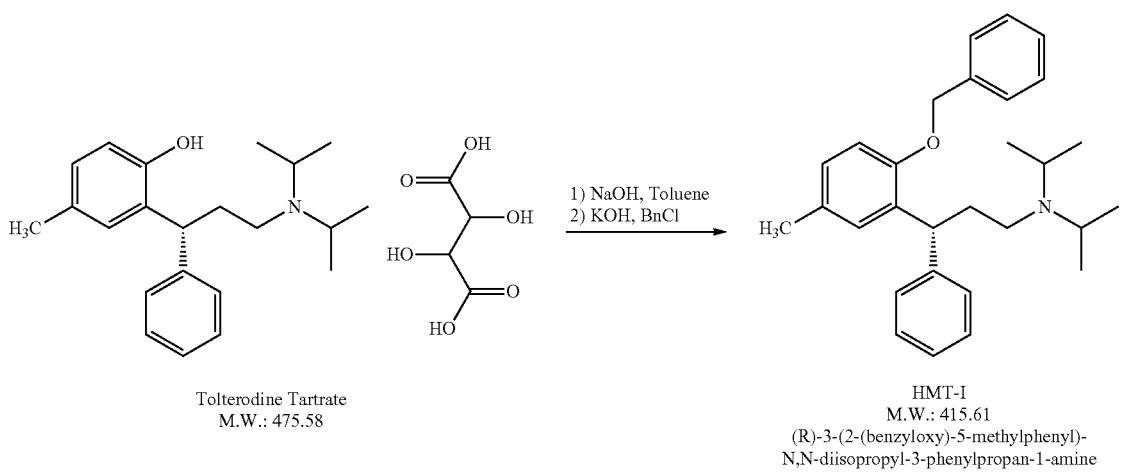

Tolterodine Tartrate
M.W.: 475.58

HMT-I
M.W.: 415.61
(R)-3-(2-(benzyloxy)-5-methylphenyl)-
N,N-diisopropyl-3-phenylpropan-1-amine Water (55 L) was charged into the reactor followed by sodium hydroxide (2.75 Kg) and allowed to stir until clear solution. Toluene (77 L) and tolterodine tartrate (11.0 Kg) were charged to the reactor and stirred for 1 h at 30-35° C.; layers were separated. Aqueous layer was extracted with toluene (33.0 L). Combined organic layers were distilled out at 70° C. under reduced pressure followed by removal of traces of toluene by DMF (5.5 L) distillation to get oily mass. Oil was dissolved in DMF (38.5 L) at 25° C. Potassium hydroxide (2.2 Kg) was charged at 25° C. Benzyl chloride (3.51 Kg) was added into the reaction mass and allowed to stir at 25° C. for 3 h. After completion; reaction mass was filtered out and washed with DMF (22 L). Combined organic filtrates were allowed to cool at 10° C. Water (~7.5 L) was added slowly maintaining temp 10° C. until turbidity appeared; seeding (55 g) was applied and reaction mass was allowed to stir for 1 h followed by addition of remaining water (55 L) at 10° C. Reaction mass was allowed to stir for 10 h at 10° C. for complete crystallization. Solid was filtered out and washed with precooled mixture of DMF (5.5 L) and water (5.5 L) and was dried under reduced pressure for about 6 h at 35° C. Dry (9.5 Kg).

Preparation of Benzyl Desfesoterodine Fumarate (HMT-IIB Fumarate) from Benzyl Tolterodine (HMT-I)

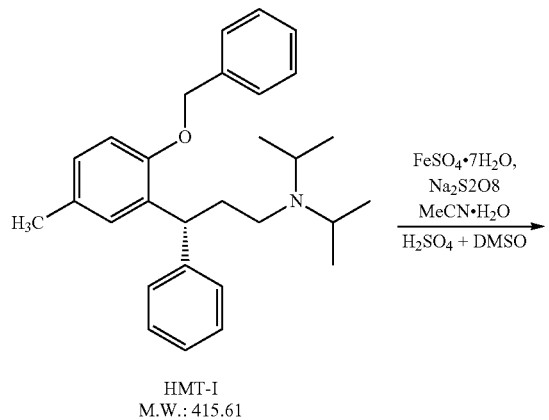

HMT-I
M.W.: 415.61

FeSO$_4$·7H$_2$O,
Na$_2$S$_2$O$_8$
MeCN·H$_2$O
H$_2$SO$_4$ + DMSO

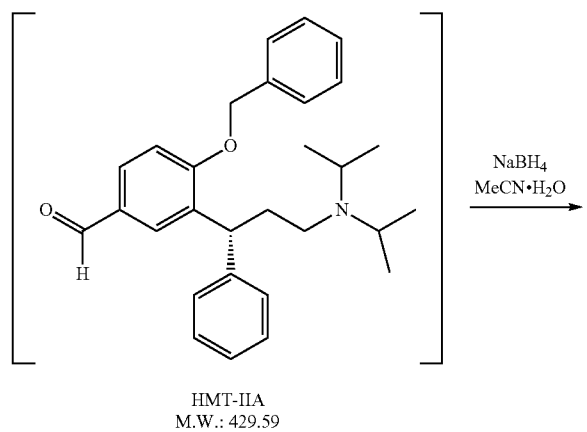

HMT-IIA
M.W.: 429.59

NaBH$_4$
MeCN·H$_2$O

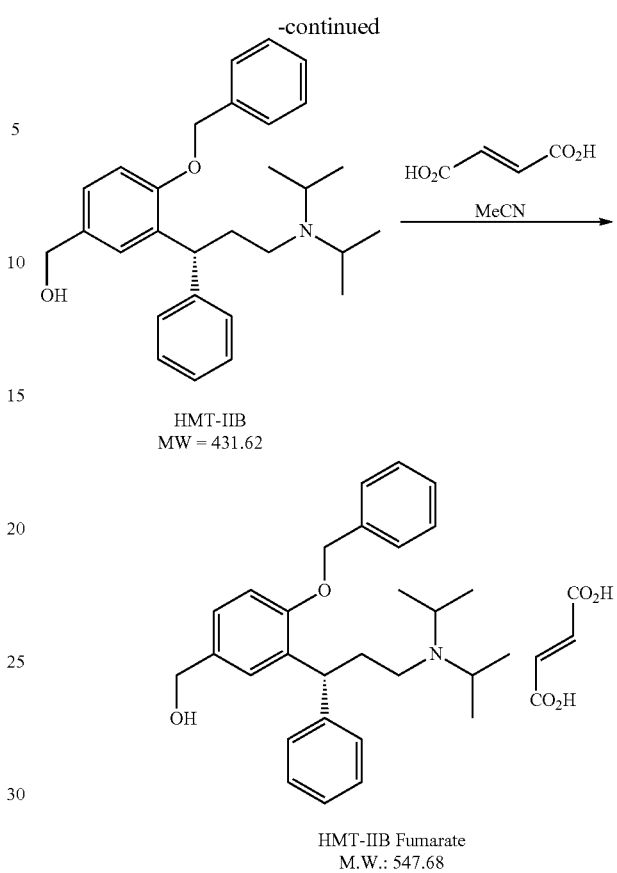

HMT-IIB
MW = 431.62

HMT-IIB Fumarate
M.W.: 547.68

Water (86 L) and HMT-I (10.11 Kg) were charged into the reactor at 30° C. Acetonitrile (101 L) was charged followed by adding aqueous solution of sulfuric acid (2.14 Kg sulfuric acid in 10.11 L water) into the reaction mass. DMSO (19.01 Kg) was charged. Ferrous sulphate heptahydrate (16.88 Kg) and sodium persulphate (21.74 Kg) were charged into the reaction mass at 30° C. Reaction mass was stirred for 2.5 h at 80° C. After completion of reaction; reaction mass was cooled to 30° C. Sodium carbonate (10.62 Kg) was charged lot wise (2.12 Kg×5) over a period of 1.5 h and stirred for 1 h. Reaction mass was filtered and inorganic solid was washed twice with mixture of acetonitrile (2×30 L) and water (2×10 L). Aqueous sodium borohydride solution (0.20 Kg NaOH in 4.64 L water followed by adding NaBH4 (1.84 Kg) in aq. NaOH solution) was charged slowly into the reaction mass (filtrate obtained from oxidation step) at 25° C. within 40 min and allowed to stir between 25-30° C. for 3 h. After completion of reaction, reaction mass was quenched by aq. hydrochloric acid solution (7.58 L hydrochloric acid in 10 L water) at 25° C. followed by addition of sodium hydroxide solution (Sodium hydroxide (6.57 Kg) in water (26.27 L) at 30° C. Reaction mass was stirred for 1 h; layers were separated. Organic layer was distilled out at 60° C. under reduced pressure to get an oily mass. Aqueous layer was extracted twice with toluene (55 L). Combined toluene layers were charged to concentrated organic mass obtained from MeCN distillation and allowed to stir for about 2 h at 40° C. until dissolution. Organic mass was filtered through celite bed followed by washing with sodium chloride solution (0.05 Kg EDTA and 12.64 Kg sodium chloride in 50 L water) twice. Toluene was distilled under reduced pressure at 70° C. Crude oily mass was allowed to cool to 35° C. Acetonitrile (70 L) followed by neutral alumina (2 Kg) were added to oily mass and stirred for 1 h and filtered through the celite bed and washed with acetonitrile (20 L×2).

Fumaric acid (2.83 Kg) was added to the organic mass and allowed to heat at 75-85° C. for 2.0 hr; followed by cooling at 20° C. and stirring for 15 h. Compound was filtered and washed with acetonitrile (30 L) at 20° C. Compound was dried under reduced pressure at 50° C. for 12 h. Dry (11.1 Kg).

Alternative Process (1) for the Preparation of Benzyl Desfesoterodine Fumarate (HMT-IIB Fumarate) from Benzyl Tolterodine (HMT-I)

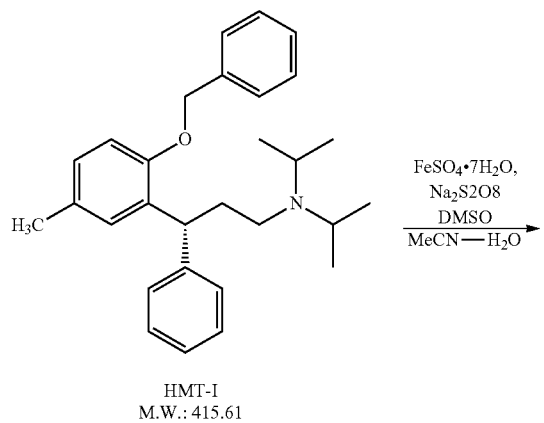

HMT-I
M.W.: 415.61

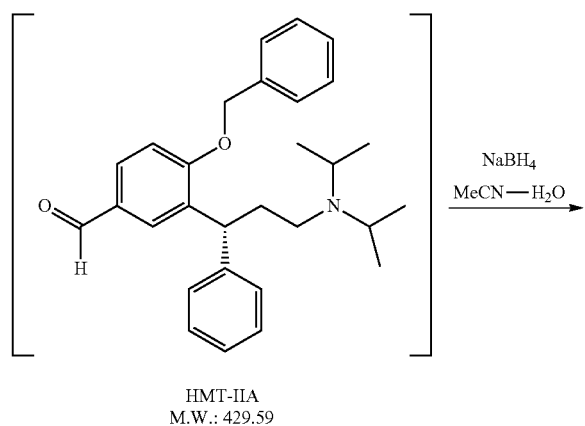

HMT-IIA
M.W.: 429.59

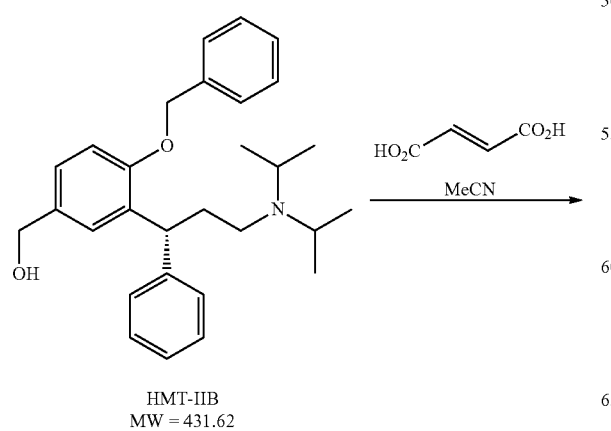

HMT-IIB
MW = 431.62

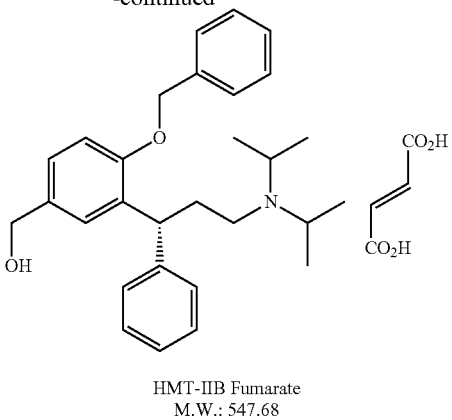

HMT-IIB Fumarate
M.W.: 547.68

Water (250 mL), acetonitrile (250 mL), ferrous sulphate heptahydrate (41.7 g; 2.5 eq) and sodium persulphate (53.57 g; 3.75 eq) were charged at 30° C. HMT-I (25 g) was charged followed by DMSO (46.88 g; 10 eq.). Reaction mass was stirred for 2.0 h at 80° C. After completion of reaction; reaction mass was cooled to 25° C. and quenched by lot wise addition of sodium carbonate (26.2 g; 4.12 eq). Reaction mass was filtered and inorganic solid was washed with mixture of acetonitrile (2×75 mL) and water (2×25 mL) Aqueous sodium borohydride solution (0.5 g NaOH in 10 mL water followed by addition of 4.54 g NaBH₄) was charged slowly into the reaction mass (filtrate obtained from oxidation step) at 25° C. and allowed to stir between 25-30° C. for 3 h. After completion of reaction, reaction mass was quenched by aq. hydrochloric acid solution (18.5 mL hydrochloric acid in 25 mL water) at 25° C. followed by addition of sodium hydroxide solution (Sodium hydroxide (16.25 g) in water (65 mL)) at 30° C. Reaction mass was stirred for 1 h; layers were separated. Organic layer was distilled out at 60° C. under reduced pressure to get an oily mass. Aqueous layer was extracted with toluene (2×140 mL). Combined toluene layers were charged to concentrated organic mass obtained from MeCN distillation. Organic mass was filtered through celite bed followed by washing with sodium chloride solution (31.25 g sodium chloride in 125 mL water) twice. Toluene was distilled under reduced pressure at 70° C. Crude oily mass obtained was dissolved in acetonitrile (250 mL) at 35° C. Fumaric acid (7 g) was added to the organic mass and allowed to heat at 75-85° C. for 2.0 hr; followed by cooling between 15-20° C. and stirred for 15 h. Compound was filtered and washed with acetonitrile (75 mL) at 20° C. Compound was dried under reduced pressure at 50° C. for 12 h. Dry (27.45 g).

Alternative Process (2) for Preparation of Benzyl Desfesoterodine Fumarate (HMT-IIB Fumarate) from Benzyl Tolterodine (HMT-I)

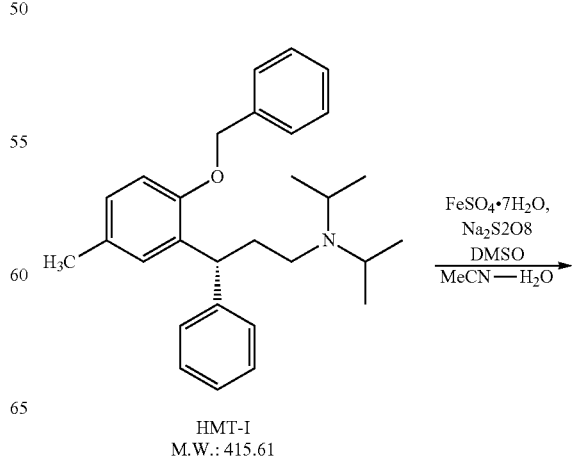

HMT-I
M.W.: 415.61

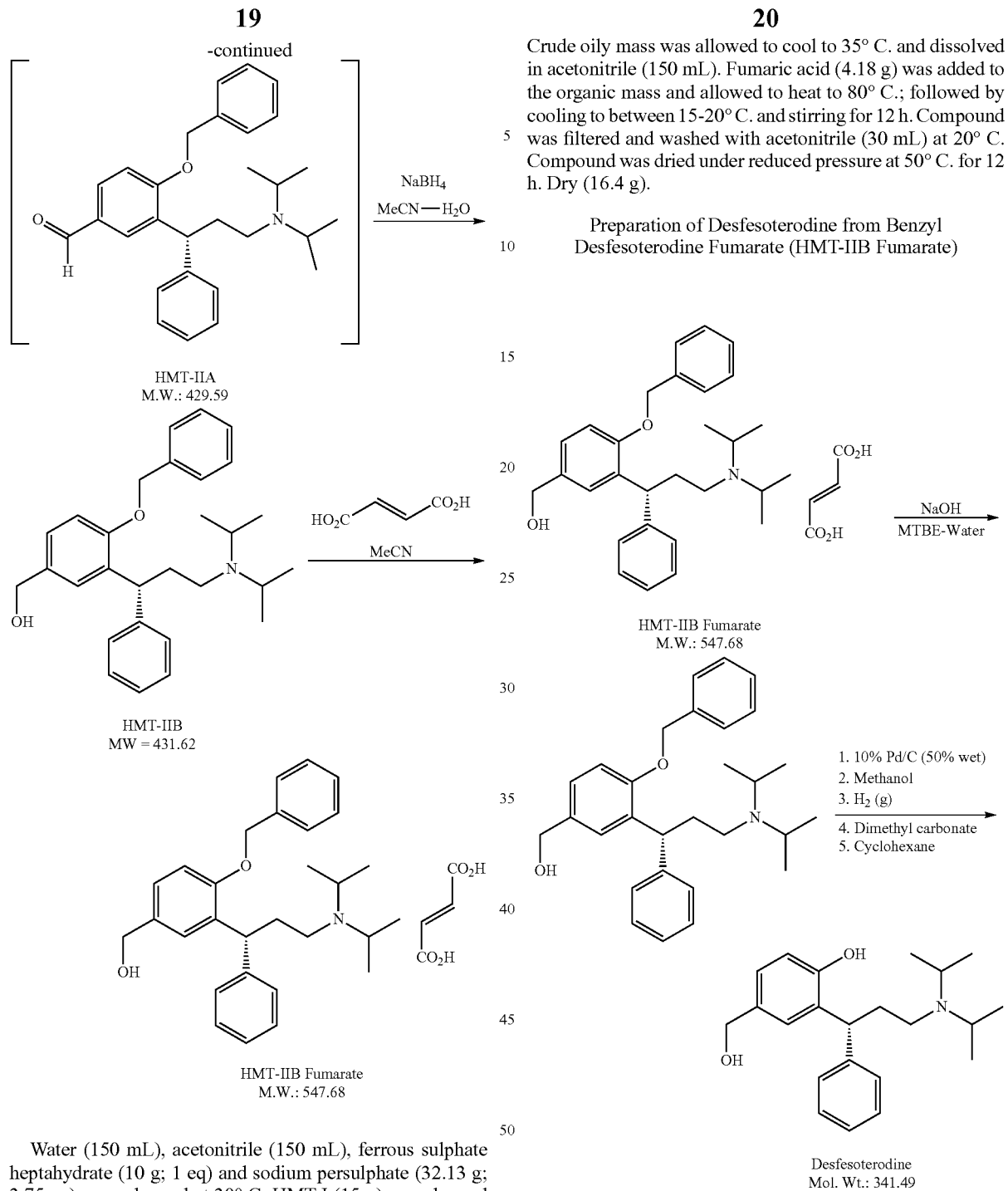

Water (150 mL), acetonitrile (150 mL), ferrous sulphate heptahydrate (10 g; 1 eq) and sodium persulphate (32.13 g; 3.75 eq) were charged at 30° C. HMT-I (15 g) was charged followed by DMSO (27.40 g). Reaction mass was stirred for 2.5 h at 80° C. After completion of reaction; reaction mass was cooled to 5° C. and quenched by 10% aq. sodium hydroxide (100 mL). Sodium borohydride (2.72 g; 2 eq) was charged slowly into the reaction mass at 5-10° C. After completion of reaction, reaction mass was quenched by concentrated hydrochloric acid (30 mL) at 20-25° C. Reaction mass was stirred for 1 h; layers were separated. Organic layer was distilled out at 60° C. under reduced pressure to get an oily mass. Aqueous layer was extracted with MTBE (150 mL) MTBE layer was charged into concentrated organic mass obtained from MeCN distillation and washed with 10% aq. $Na_2CO_3$ solution (40 mL); layers were separated. Organic layer was washed with water (150 mL) and distilled under reduced pressure at 60° C. Crude oily mass was allowed to cool to 35° C. and dissolved in acetonitrile (150 mL). Fumaric acid (4.18 g) was added to the organic mass and allowed to heat to 80° C.; followed by cooling to between 15-20° C. and stirring for 12 h. Compound was filtered and washed with acetonitrile (30 mL) at 20° C. Compound was dried under reduced pressure at 50° C. for 12 h. Dry (16.4 g).

Preparation of Desfesoterodine from Benzyl Desfesoterodine Fumarate (HMT-IIB Fumarate)

Water (50 L) followed by sodium hydroxide (3.24 Kg) were charged. MTBE (84 L) and HMT-IIB fumarate (12.0 Kg) were charged into the aq NaOH solution and stirred for 2 h between 25-30° C. Layers were separated. Aqueous layer was extracted with MTBE (36 L). Combined organic extract was distilled to get thick oily mass under reduced pressure at 55° C. Oily mass was given methanol (6 L) distillation at 55° C. to remove traces of MTBE followed by addition of methanol (96 L) and 10% Pd/C (50% wet) (1.8 Kg) at 20° C. Autoclave was flushed with nitrogen gas 3 times. Reaction was carried out at between 3-5 Kg/cm² hydrogen gas pressure for 6 h at 20° C. Reaction mass was filtered through the celite bed and the catalyst was washed with methanol (48 L). Filtrate was distilled out to remove methanol completely under reduced pressure at 35° C. Crude was given MTBE (6 L) distillation at 35° C. to remove traces of MeOH. Crude obtained was dissolved in MTBE (120 L) and extracted with aq. solution of sodium hydroxide (sodium hydroxide (1.32 Kg) in water (30 L)). Aqueous layer was given MTBE (36 L) wash. Combined organic extracts were washed with sodium chloride solution (sodium chloride (9 Kg) in Water (60 L)) followed by activated carbon treatment. Carbon was filtered through the celite bed and washed with MTBE (24 L). MTBE was distilled out to get an oily mass under reduced pressure at 50° C. followed by stripping with cyclohexane (6 L) at 50° C. Crude was allowed to cool to 40° C.; dissolved in dimethyl carbonate (6 L) and cyclohexane (60 L) at 55° C. followed by cooling and stirring at between 15-20° C. for 16 h. Crystallization mass was further cooled to 0-5° C. and stirred for 3 hours. Solid was filtered and washed with cyclohexane (36 L). Wet Desfesoterodine (on anhydrous basis) was again purified with Dimethyl carbonate (6 L) and cyclohexane (60 L) following the same procedure and dried under reduced pressure at 30° C. Dry (5.85 Kg).

Alternative Process for the Preparation of Desfesoterodine from Benzyl Desfesoterodine Fumarate (HMT-IIB Fumarate)

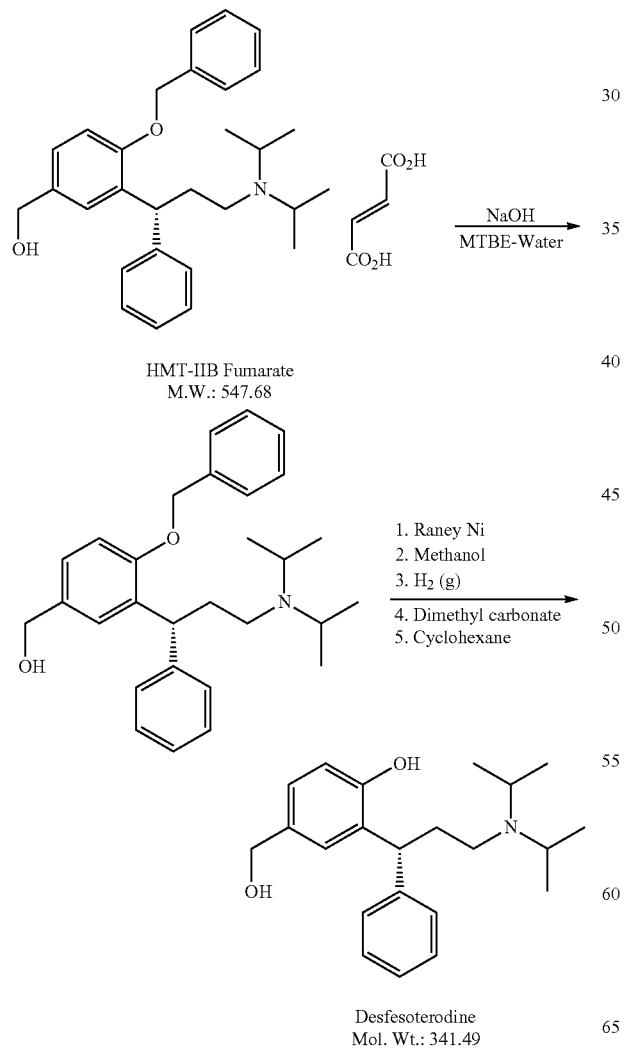

Water (60 mL) followed by sodium hydroxide (3.78 g) were charged. MTBE (100 mL) and HMT-IIB fumarate (14 g) were charged into the aq NaOH solution and stirred for 2 h between 25-30° C. Layers were separated. Aqueous layer was extracted with MTBE (42 mL). Combined organic extract was distilled to get a thick oily mass under reduced pressure at 55° C. Oily mass was given methanol (7 mL) distillation at 55° C. to remove traces of MTBE followed by addition of methanol (112 mL) and Raney Ni (1.25 g) at 15° C.±3. Autoclave was flushed with nitrogen gas 3 times. Reaction was carried out at between 3-5 Kg/cm² hydrogen gas pressure for 8 h at 15° C.±3. Reaction mass was filtered through the celite bed and the catalyst was washed with methanol (56 mL). Filtrate was distilled out to remove methanol completely under reduced pressure at 35° C. Crude was given MTBE (56 mL) distillation at 35° C. to remove traces of MeOH. Crude obtained was dissolved in MTBE (140 mL) and extracted with aq. solution of sodium hydroxide (sodium hydroxide (1.54 g) in water (35 mL)). Aqueous layer was given MTBE (42 mL) wash. Combined organic extracts were washed with sodium chloride solution (sodium chloride (10.5 g) in water (70 mL)) followed by activated carbon treatment. Carbon was filtered through the celite bed and washed with MTBE (28 mL). MTBE was distilled out to get the oily mass under reduced pressure at 50° C. followed by stripping with cyclohexane (7 mL) at 50° C. Crude was allowed to cool to 40° C.; dissolved in dimethyl carbonate (7 mL) and cyclohexane (70 mL) at 55° C. followed by cooling and stirring at between 15-20° C. for 16 h. Crystallization mass was further cooled down to 0-5° C. and stirred for 3 hours. Solid was filtered and washed with cyclohexane (42 mL). Wet Desfesoterodine was again purified with dimethyl carbonate (7 mL) and cyclohexane (70 mL) following the same procedure and dried under reduced pressure at 30° C. Dry (6.5 g).

What is claimed is:

1. A succinate salt of Desfesoterodine.

2. The succinate salt of Desfesoterodine of claim 1, wherein the succinate salt of Desfesoterodine is isolated.

3. The succinate salt of Desfesoterodine of claim 1, wherein the succinate salt is in an anhydrous form.

4. The succinate salt of claim 1, wherein the succinate salt of Desfesoterodine is in solid form.

5. The succinate salt of Desfesoterodine of claim 1, wherein the molar ratio between Desfesoterodine and succinic acid is 1:1 to 1:1.5, respectively.

6. The succinate salt of Desfesoterodine of claim 1, having a chemical purity of at least 95%, >98%, or >99% by HPLC/UV (area %).

7. The succinate salt of Desfesoterodine of claim 1, wherein the salt is in a crystalline form.

8. The succinate salt of Desfesoterodine of claim 7, wherein the crystalline form of Desfesoterodine succinate is designated as Form S1 and is characterized by data selected from the group consisting of:

an X-ray powder diffraction pattern having peaks at 7.4, 16.8, 18.0, 21.7 and 27.4 degrees two theta±0.2 degrees two theta;

an X-ray powder diffraction pattern substantially as depicted in FIG. 5;

and combinations thereof.

9. The succinate salt of Desfesoterodine of claim 8, wherein the crystalline form of Desfesoterodine succinate is an X-ray powder diffraction pattern having any one, two, three, four or five additional peaks selected from peaks at 9.3, 12.2, 14.6, 19.6 and 24.5 degrees two theta±0.2 degrees two theta;

a DSC curve having an endothermic peak at about 169° C.±2, a DSC curve substantially as depicted in FIG. 3;

and combinations thereof.

10. The succinate salt of Desfesoterodine of claim 8, wherein the crystalline form of Desfesoterodine succinate is anhydrous.

11. A malate salt of Desfesoterodine.

12. The malate salt of Desfesoterodine of claim 11, wherein the salt is isolated.

13. The malate salt of Desfesoterodine of claim 11, wherein the salt is in solid form.

14. The malate salt of Desfesoterodine of claim 11, wherein the molar ratio between Desfesoterodine and malic acid is 1:1 to 1:1.5, respectively.

15. The malate salt of Desfesoterodine of claim 11, having a chemical purity of >95%, >98%, or >99% by HPLC/UV (% area).

16. The malate salt of Desfesoterodine of claim 11, wherein the Desfesoterodine malate is in a crystalline form.

17. The malate salt of Desfesoterodine of claim 16, wherein the crystalline form of Desfesoterodine malate is designated as Form M1 and is characterized by data selected from the group consisting of:

an X-ray powder diffraction pattern having peaks at 7.2, 16.4, 19.8, 21.3 and 29.6 degrees two theta±0.2 degrees two theta;

an X-ray powder diffraction pattern substantially as depicted in FIG. 6;

and combinations thereof.

18. The malate salt of Desfesoterodine of claim 17, wherein the crystalline form of Desfesoterodine malate is further characterized by data selected from the group consisting of:

an X-ray powder diffraction pattern having any one, two, three, four or five additional peaks selected from peaks at 12.2, 14.5, 18.5, 23.1 and 24.5 degrees two theta±0.2 degrees two theta;

a DSC curve having an endothermic peak at about 141° C., a DSC curve substantially as depicted in FIG. 4;

and combinations thereof.

19. A process for preparing other Desfesoterodine salts comprising preparing any one of the Desfesoterodine salts according to any one of claim 1, 8, 11, or 17, and converting that salt to said other Desfesoterodine salt.

20. A pharmaceutical composition comprising any one or a combination of the Desfesoterodine salts according to any one of claim 1, 8, 11, or 17.

21. A pharmaceutical formulation comprising any one or a combination of the Desfesoterodine salts according to any one of claim 1, 8, 11, or 17 and at least one pharmaceutically acceptable excipient.

22. A process for preparing a pharmaceutical formulation comprising combining any one or a combination of the Desfesoterodine salts according to any one of claim 1, 8, 11, or 17 and at least one pharmaceutically acceptable excipient.

23. A method for treating urinary incontinence and overactive bladder in a person suffering therefrom comprising administering to the person a therapeutically effective amount of the Desfesoterodine salt of any one of claim 1, 8, 11, or 17.

24. The succinate salt of Desfesoterodine of claim 5, wherein the molar ratio between Desfesoterodine and succinic acid is about 1:1.

25. The malate salt of Desfesoterodine of claim 14, wherein the molar ratio between Desfesoterodine and malic acid is about 1:1.

26. A method for treating urinary incontinence and overactive bladder in a person suffering therefrom comprising administering to the person a therapeutically effective amount of the pharmaceutical formulation of claim 21.

27. A process for preparing a pharmaceutical formulation comprising combining the pharmaceutical composition of claim 20 and at least one pharmaceutically acceptable carrier.

* * * * *